US00PP21609P2

(12) United States Plant Patent
Saul

(10) Patent No.: US PP21,609 P2
(45) Date of Patent: Jan. 4, 2011

(54) ***DIANTHUS* PLANT NAMED 'BEDAZZLED'**

(50) Latin Name: *Dianthus gratianopolitanus*
Varietal Denomination: Bedazzled

(75) Inventor: Richard G. Saul, Cleveland, GA (US)

(73) Assignee: Itśaal Plants, LLC, Alpharetta, GA (US)

( * ) Notice: Subject to any disclaimer, the term of this patent is extended or adjusted under 35 U.S.C. 154(b) by 0 days.

(21) Appl. No.: 12/587,165

(22) Filed: Oct. 2, 2009

(51) Int. Cl.
*A01H 5/00* (2006.01)

(52) U.S. Cl. ..... Plt./276
(58) Field of Classification Search ..... Plt./276
See application file for complete search history.

*Primary Examiner*—Susan B McCormick Ewoldt
(74) *Attorney, Agent, or Firm*—Penny J. Aguirre

(57) ABSTRACT

A new cultivar of *Dianthus gratianopolitanus,* 'Bedazzled', characterized by its blue-grey foliage, its tight, compact habit throughout year, its flowers that are light pink in color with a distinct burgundy eye that bloom sporadically throughout the year with 2 heavy flushes of bloom for 4 weeks in spring and 4 weeks in fall in Georgia.

2 Drawing Sheets

Botanical classification: *Dianthus gratianopolitanus.*
Variety denomination: 'Bedazzled'.

BACKGROUND OF THE INVENTION

The present invention relates to a new and distinct cultivar of *Dianthus* plant, botanically known as *Dianthus gratianopolitanus* 'Bedazzled' and will be referred to hereinafter by its cultivar name, 'Bedazzled'. The new cultivar represents a new cultivar of cheddar pinks, an herbaceous perennial grown for landscape use.

'Bedazzled' was discovered in a container block in the Inventor's nursery in Alpharetta, Ga. in August of 2007. The new cultivar derived as a naturally occurring branch mutation of *Dianthus gratianopolitanus* 'Bewitched' (U.S. Plant Pat. No. 13,159).

Asexual reproduction of the new cultivar was first accomplished by the Inventor using stem cuttings in August of 2007 in Dahlonega, Ga. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Bedazzled' as unique from all other varieties of *Dianthus* known to the Inventor.

1. 'Bedazzled' exhibits foliage that is blue-grey in color.
2. 'Bedazzled' exhibits a tight, compact habit throughout the year.
3. 'Bedazzled' exhibits flowers that are light pink in color with a distinct burgundy eye.
4. 'Bedazzled' blooms sporadically throughout the year with 2 heavy flushes of blooms for 4 weeks in spring and 4 weeks in fall in Georgia.

In comparison to its parent plant, 'Bewitched', 'Bedazzled' differs in having a plant habit that remains tighter throughout the season in warm regions of the U.S. and in having flowers that are pink in color with a burgundy eye, whereas 'Bewitched' exhibits flowers that are pale pink and lack a distinct eye. 'Bedazzled' can be most closely compared to *Dianthus gratianopolitanus* cultivars 'Firewitch' and 'Bath's Pink' (both unpatented). 'Firewitch' is similar to 'Bewitched' in having tightly mounded blue-grey foliage, however 'Firewitch' differs from 'Bewitched' in having flowers that are bright magenta in color. 'Bedazzled' is similar to 'Bath's Pink' in having blue-grey foliage, however 'Bath's Pink' differs from 'Bedazzled' in having a looser plant habit and in having flowers that are pink in color and lack the burgundy colored eye zone of 'Bedazzled'.

BRIEF DESCRIPTION OF THE DRAWING

The accompanying colored photographs illustrate the overall appearance and distinct characteristics of the new *Dianthus.* The photographs in the figures were taken of a plant about one year in age as grown outdoors in a trial garden in Alpharetta, Ga.

Figure 1:
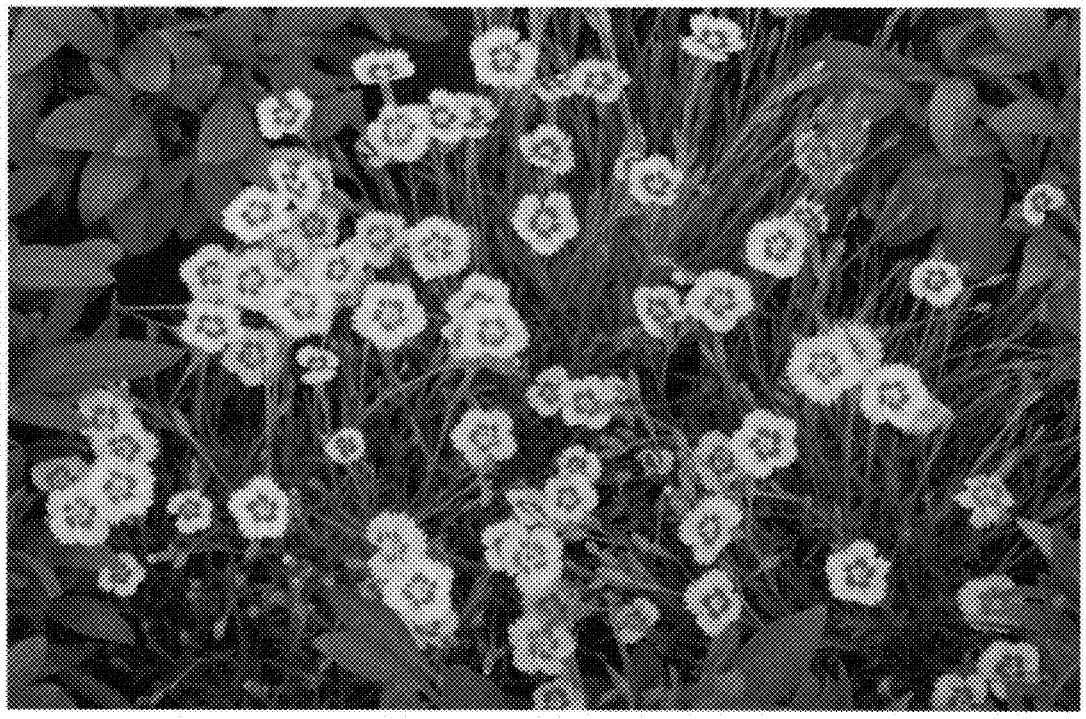
FIG. 1 provides a view of the plant habit of 'Bedazzled' in bloom.
Figure 2:
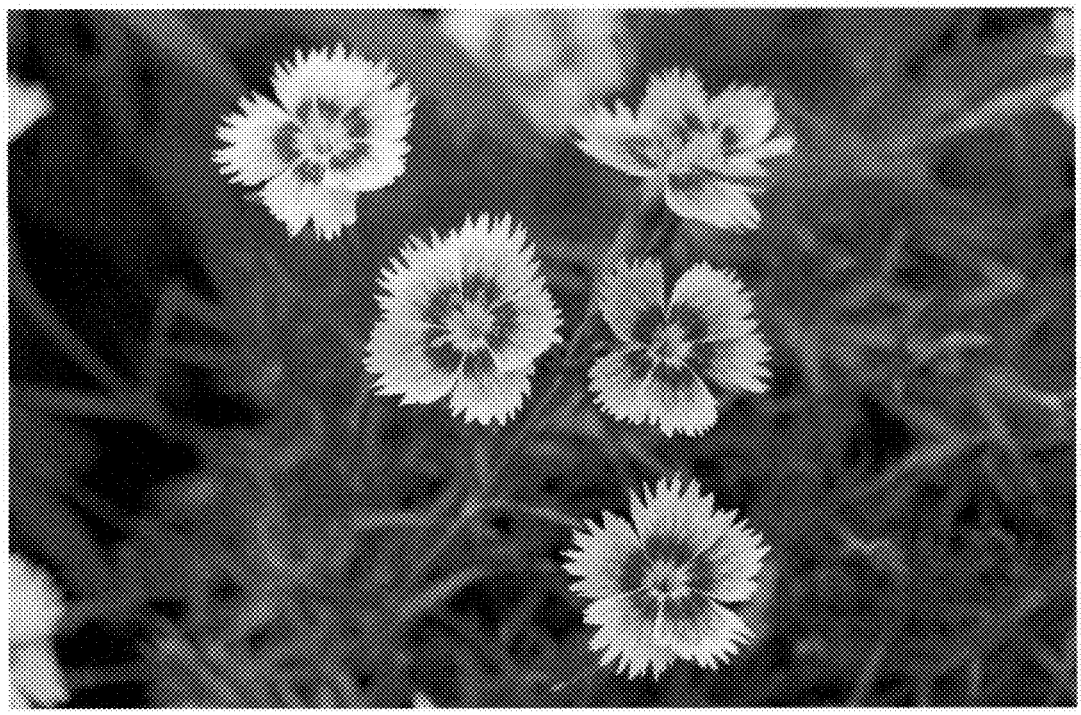
FIG. 2 provides a close-up view of the flowers of 'Bedazzled'.

The colors in the photographs may differ slightly from the color values cited in the detailed botanical description, which accurately describe the colors of the new *Dianthus.*

DETAILED BOTANICAL DESCRIPTION

The following is a detailed description of a plant about one year in age of the new cultivar as grown outdoors in a one-gallon container in Dahlonega, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms sporadically throughout the year with 2 heavy flushes of bloom for 4 weeks in spring and 4 weeks in fall in Georgia.

*Plant habit.*—Herbaceous perennial, evergreen, tightly mounded foliage with upright flower scapes.

*Height and spread.*—An average of 20 cm in height and about 30 cm in width.

*Hardiness.*—At least in U.S.D.A. Zones 4 to 9.

*Diseases and pests.*—No susceptibility or resistance to diseases or pests has been observed.

*Root description.*—Fibrous.

Growth and propagation:

*Propagation.*—Stem cuttings.

*Root initiation.*—Cuttings root in about 2 weeks in the summer at 25° C. and winter at 20° C.

*Root development.*—A cutting is fully developed in a 2-inch plug in 5 to 6 weeks in summer and 6 to 7 weeks in winter.

*Growth rate.*—Moderate.

Stem description:

*Stem strength.*—Strong and held upright.

*Shape.*—Oval, solid swollen at nodes.

*Stem color.*—Young; 145A to 145C, mature; 138A, bark; N199B with nodes 161A.

*Stem size.*—Average of 1.7 mm in diameter and 15 cm in length (including peduncle).

*Stem surface.*—Finely puberulent imparting a glaucous appearance when mature, bark-like on basal stems.

*Branching habit.*—Numerous dense branches emerge in whorls from stout woody stems, about 200 lateral branches as grown in a one-gallon container, continuously produced during bloom season.

Foliage description:

*Leaf division.*—Simple.

*Leaf shape.*—Linear.

*Leaf base.*—Blunt, clasping to stem.

*Leaf apex.*—Narrowly acute.

*Leaf margin.*—Entire, minute rough hairs.

*Leaf venation.*—Linear, not conspicuous, color same as leaf color.

*Leaf attachment.*—Sessile, clasping.

*Leaf arrangement.*—Opposite.

*Leaf surface.*—Glaucous on upper and lower surfaces.

*Leaf color.*—Newly emerged and mature upper and lower surface; 189A with glaucous coating of 189B basal clasping portion 138D.

*Leaf size.*—Average of 3.8 cm in length and 3 mm in width with basal portion clasping leaf about 3 mm width and length.

*Foliage fragrance.*—None.

Flower description:

General description:

*Inflorescence type.*—Solitary and occasionally pairs of salviform flowers at terminus of lateral branches.

*Lastingness of inflorescence.*—About 4 days.

*Fragrance.*—Mildly sweet.

*Quantity of flowers.*—About 150 flowers per one-gallon plant, produced in succession with an average of 20 flowers open at one time.

*Flower type.*—Salviform.

*Flower size.*—About 2.5 cm in diameter and 2.3 cm in depth.

*Flower buds.*—About 1.3 cm in height and 3 mm in diameter, oblong in shape, color 138A to 138B with apex 76D.

*Peduncle.*—An average of 1 cm in length and 1 mm in diameter, 138A in color, surface is puberulent and appears glaucous.

*Pedicel.*—Flowers are sessile to peduncle.

*Petals.*—4, limb is obdeltoid in shape, glabrous surface, rounded apex, margins are serrated along apex and sides and entire at base, limb is about 1.2 cm in width and 1 cm in length, claw (enclosed in calyx)) is an average of 1 cm in length and 2 mm in width, color when opening upper surface; claw 144D, limb 76D with center portion marked with striations of 72A and eye zone N79B, color when opening lower surface; claw 144D, limb 76D and lightly suffused at base with N80D, color when mature open upper surface; claw 144D, limb 75D slightly diffused with 75A and 75B and eye zone 72A, color when mature lower surface; claw 144D, limb 76D and slightly suffused with N80C, not persistent.

*Calyx.*—Cylindrical in shape, fused sepals with un-fused apex, puberulent surface, average of 1.5 cm in length and 3 mm in width, 138A to 138C in color, persistent and dries to about 164C in color.

*Sepals.*—5, fused, the triangle-shaped tip at apex are un-fused and about 2 mm in height and 3 mm in width.

*Epicalyx.*—Comprised of 5 involucre bracts; oblong to ovate in shape with truncate base and caudate apex, about 6 mm in length and 2.5 mm in width, 138B to 138C in color, puberulent surface.

Reproductive organs:

*Gynoecium.*—Pistil; about 2 cm in length at maturity, extended beyond petals, styles; N155C in color, crystalline in appearance, about 1.9 cm in length, stigma; color N155C flushed with 91D in and curled, ovary; superior to stamens and inferior to pistils, oblong in shape, 1 cm in length and 3 mm in width, 144A in color.

*Androcoecium.*—Stamens; 10, un-fused, about 7 mm in length, filament; 145C in color, about 6 mm in length, very fine and crystalline in appearance, anthers; N80C in color, dorsifixed, oblong in shape, about 2 mm in length and 0.7 mm in width, pollen; not discernable.

*Fruit and seed.*—Fruit; a capsule formed by calyx, development of seeds was not observed.

It is claimed:

1. A new and distinct cultivar of *Dianthus* plant named 'Bedazzled' as herein illustrated and described.

* * * * *